United States Patent [19]

Mayes et al.

[11] Patent Number: 4,759,838

[45] Date of Patent: Jul. 26, 1988

[54] CONTAINER FOR AN ELECTROPHORETIC SUPPORT MEDIUM

[75] Inventors: David G. Mayes, Beaumont; James R. M. Sanford, Vidor; Eric H. Petersen, Beaumont, all of Tex.

[73] Assignee: Helena Laboratories Corporation, Beaumont, Tex.

[21] Appl. No.: 356

[22] Filed: Jan. 5, 1987

[51] Int. Cl.[4] .................. B65D 83/30; B65D 6/00; G01N 27/26

[52] U.S. Cl. ........................... 204/299 R; 206/454; 206/565; 220/4 B

[58] Field of Search ............... 204/299 R, 182.8; 206/454, 455, 456, 564, 565; 220/4 B, 4 E, 339

[56] References Cited

U.S. PATENT DOCUMENTS

| | | | |
|---|---|---|---|
| 3,479,265 | 11/1959 | Elevitch | 204/182.8 |
| 3,482,943 | 12/1969 | Csizmas et al. | 422/56 |
| 3,489,265 | 1/1970 | Puente | 220/339 X |
| 3,523,863 | 8/1970 | Juhos | 428/195 |
| 3,615,006 | 10/1971 | Freed | 206/454 |
| 3,695,424 | 10/1972 | Cristy et al. | 206/455 |
| 3,710,975 | 1/1973 | Jansen | 220/339 |
| 3,725,004 | 4/1973 | Johnson et al. | 436/515 |
| 3,756,393 | 9/1973 | Markwitz | 206/456 |
| 3,766,047 | 10/1973 | Elevitch | 204/299 R |
| 3,856,656 | 12/1974 | Brink | 204/299 R |
| 3,875,045 | 4/1975 | Bergrahm et al. | 204/299 R |
| 4,011,350 | 3/1977 | Markovits | 427/2 |
| 4,077,515 | 3/1978 | Shoberg | 206/456 |
| 4,314,897 | 2/1982 | Monte et al. | 204/299 R |
| 4,511,038 | 4/1985 | Miller et al. | 206/454 |
| 4,619,364 | 10/1986 | Czopor, Jr. | 206/379 |

FOREIGN PATENT DOCUMENTS 2216299 1/1973 Fed. Rep. of Germany ... 204/182.8

Primary Examiner—John F. Niebling
Assistant Examiner—John S. Starsiak, Jr.
Attorney, Agent, or Firm—Cullen, Sloman, Cantor, Grauer, Scott & Rutherford

[57] ABSTRACT

A container for protecting and enclosing an electrophoretic support medium is disclosed. The container includes a top portion and a bottom portion, which when closed sealingly engage one another to form a substantially air-tight cavity therein. The bottom portion has a recess formed therein for accommodating the support medium and at least a portion of the recess has a substantially smooth planar surface. The bottom recess is defined by a protruding continuous rim which has a plurality of nubs protruding into said recess and engagable with the base sheet of the support medium, whereby the support medium is retained within the recess.

11 Claims, 2 Drawing Sheets

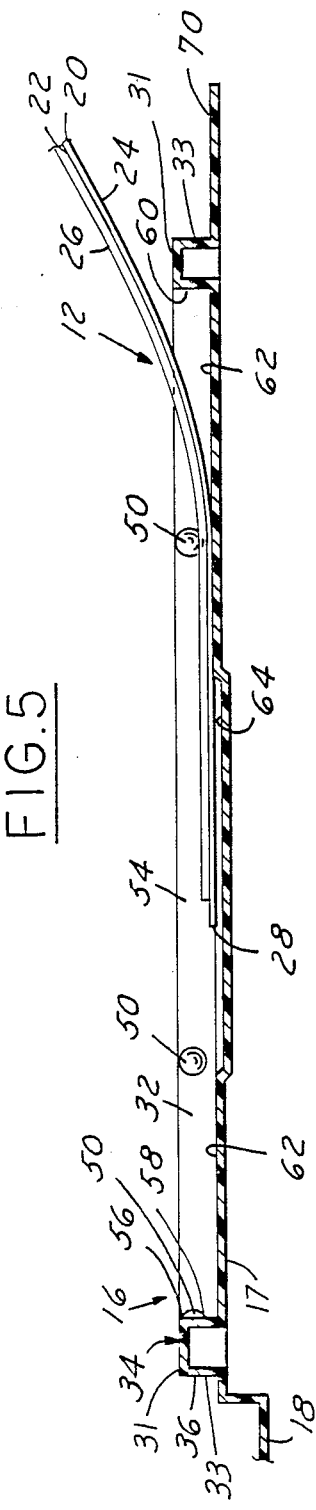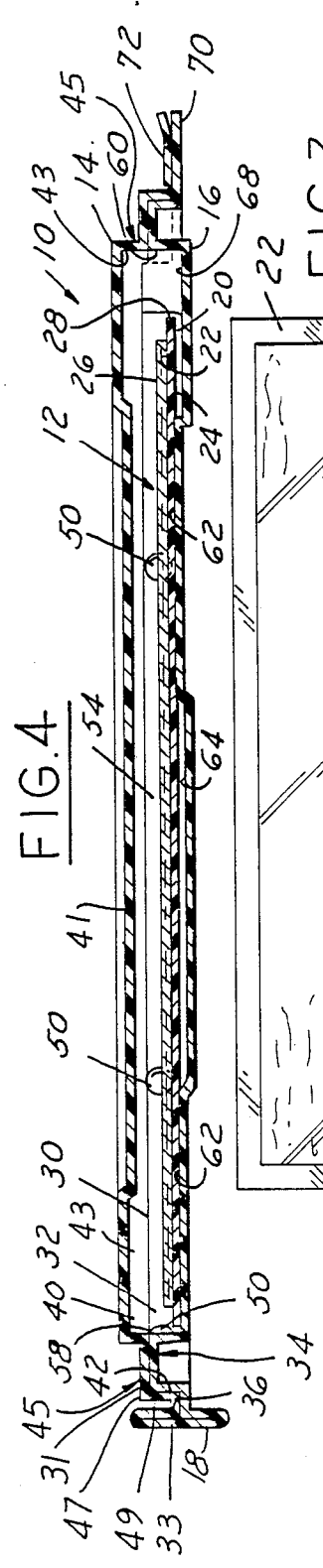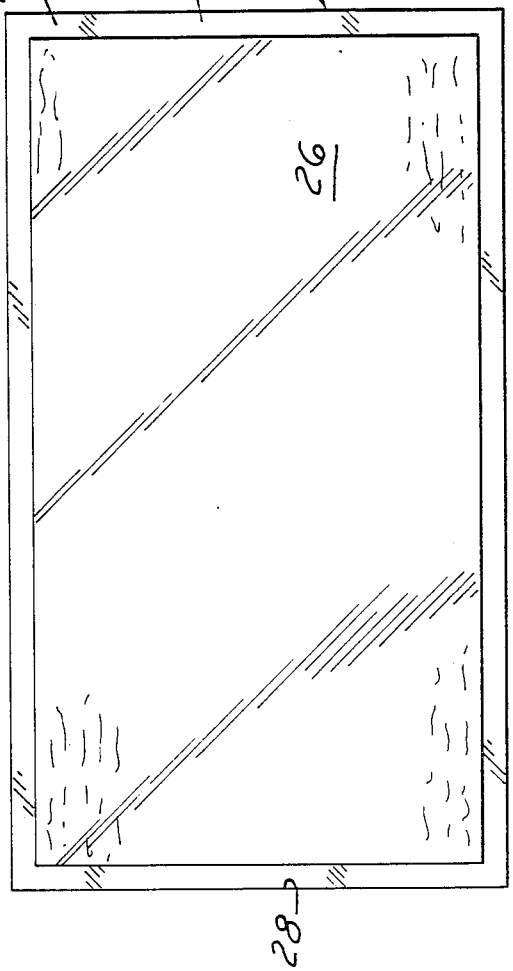

CONTAINER FOR AN ELECTROPHORETIC SUPPORT MEDIUM

FIELD OF THE INVENTION

The present invention relates generally to electrophoresis and particularly to a container for storing and protecting an electrophoretic support medium contained therein.

BACKGROUND OF THE INVENTION

It is known that an analysis of ionizable compounds, such as proteins, can be made by subjecting a sample, of for example blood, to an electrical potential as taught in U.S. Pat. Nos. 3,407,133 (Oliva et al.), 3,479,265 (Elevitch) and 3,875,045 (Bergrahm et al.). The sample to be analyzed by electrophoresis is placed on a suitable support medium, such as a gel, of the types disclosed in U.S. Pat. No. 3,725,004 (Johnson et al.). Such support medium may include, for example: (1) aqueous solutions of agar or agarose as disclosed in U.S. Pat. Nos. 3,281,409 (Blethen), 3,335,127 (Polson), 3,362,884 (Morse) and 3,766,047 (Elevitch); (2) synthetic polymeric gelling agents as disclosed in U.S. Pat. No. 3,046,201 (White et al.); and (3) cellulose and cellulose acetate as disclosed in U.S. Pat. No. 3,360,440 (Haab et al.). However, such containers have required secure retention of the electrophoretic support medium within the container to prevent the support medium from coming in contact with any part of the container to prevent flaws, such as marks or cracks, from being formed in the support medium. Such flaws are aggravated by shrinkage of the support medium caused by dehydration as disclosed, for example, in U.S. Pat. No. 4,314,897 (Monte et al.).

SUMMARY OF THE INVENTION

In contrast to the prior art containers for storing and protecting an electrophoretic support medium from physical damage and dehydration acknowledged above, the container of the present invention provides a means for securely retaining the support medium within the container by the use of a plurality of nubs positioned within the container.

The container for an electrophoretic support medium of the present invention includes a top portion and a bottom portion, which when closed sealingly engage with one another to protect and enclose a support medium having a base sheet with at least two opposed major surfaces and a layer of an electrophoretic gel adhered to one of the major surfaces of the base sheet. The bottom portion of the container has a recess formed therein for accommodating the support medium. The recess has two opposed sides, a back side, a front side and a bottom. At least one nub protrudes from each of the opposed sides of the recess into the recess and are spaced apart from the bottom of the recess. The nubs are engageable with the base sheet of the support medium so that when the support medium is placed in the recess between the nubs and the bottom of the recess, the support medium may be retained therein.

In a preferred embodiment of the present invention, at least two nubs protrude from each opposed side of the recess. In addition, at least two nubs may protrude from the back side of the recess.

BRIEF DESCRIPTION OF THE DRAWINGS

The various features, benefits, and advantages of the present invention will become more apparent by reading the following detailed description in conjunction with the drawings where like reference numerals identify corresponding components, and:

FIG. 3 is a plan view of the electrophoretic support medium with a layer of an electrophoretic gel adhered to a base sheet;

FIG. 4 is an enlarged, side cross-sectional view of the container of FIG. 1 when in a closed position, taken generally along the line 4—4 of FIG. 1 and illustrating retention of the electrophoretic support medium therein by a plurality of nubs; and FIG. 5 is an enlarged, side fragmentary view of the bottom portion of the container, in section, and taken generally along the line 5—5 of FIG. 1 illustrating insertion of the electrophoretic support medium in the recess of the bottom portion between the nubs and the bottom of the recess.

DETAILED DESCRIPTION OF THE PREFERRED EMBODIMENT

Figure 1:
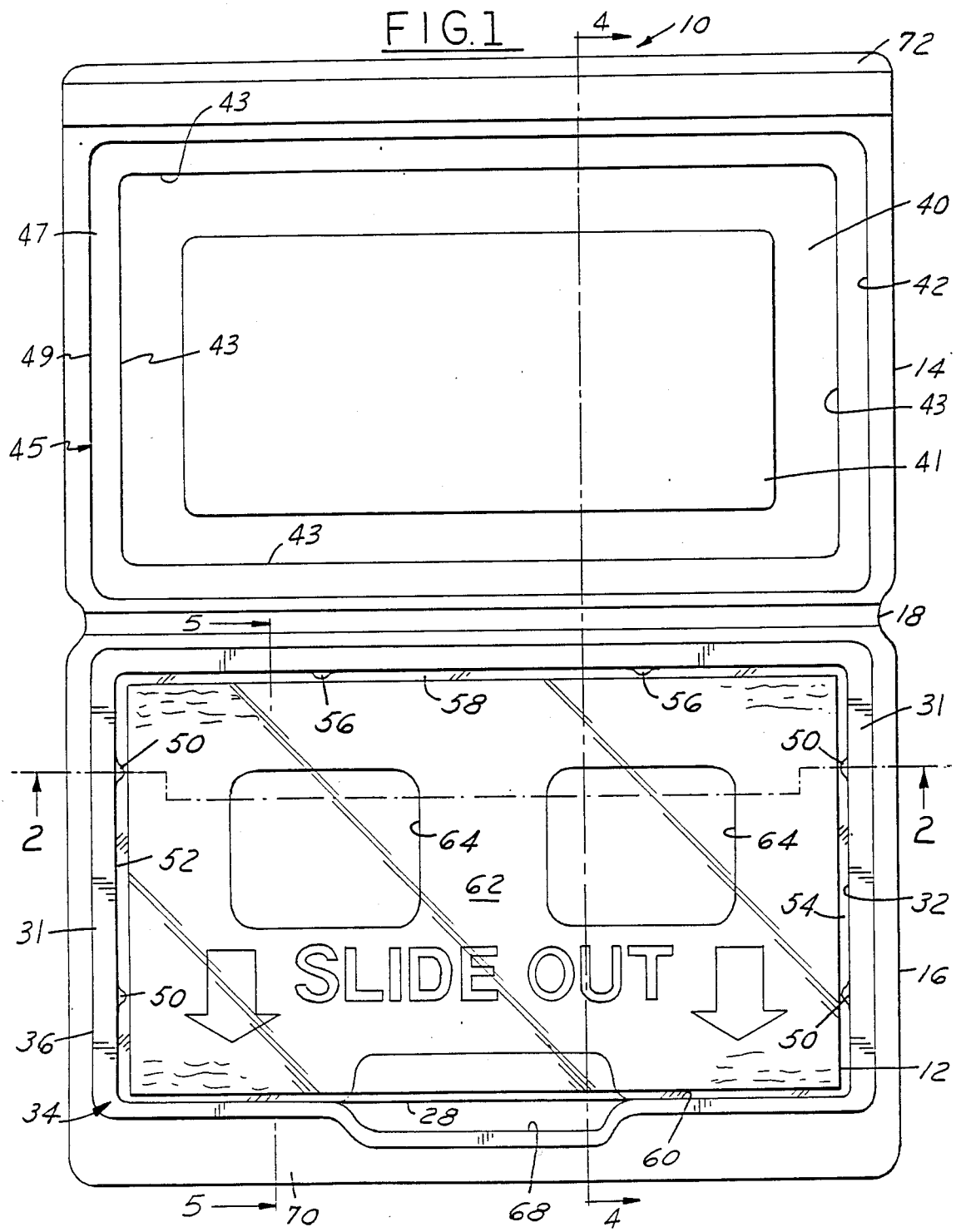
FIG. 1 is a plan view of the container of the present invention, with the container in an opened position and with the electrophoretic support medium retained in the bottom portion thereof.

Referring to FIG. 1 of the drawings, the container of the present invention, generally designated 10, for protecting and enclosing an electrophoretic support medium 12 is illustrated. The container 10 includes a top portion 14 and a bottom portion 16, which when closed sealingly engage with one another. The top portion 14 and the bottom portion 16 are hingedly connected through a hinge portion 18 to the edges of the top and bottom portions 14, 16, to permit ease of opening and closing the container.

Figure 2:
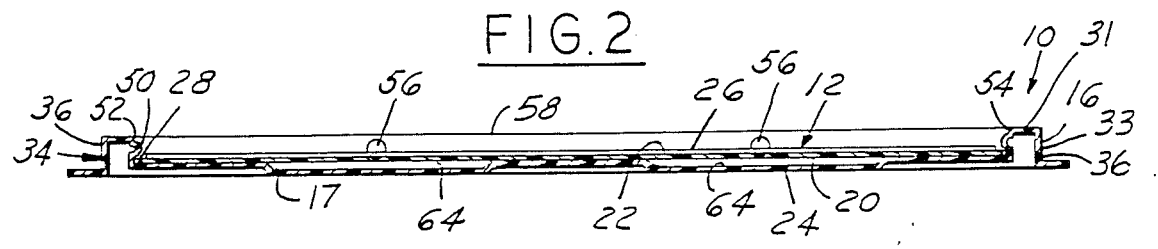
FIG. 2 is a cross-sectional view of the container illustrating the details of the layer of electrophoretic gel and the base sheet of the electrophoretic support medium taken in the direction of arrows 2—2 of FIG. 1.

As illustrated in FIG. 2 and in greater detail in FIG. 3, the electrophoretic support medium 12 includes a base sheet 20 which has at least two opposed major surfaces 22 and 24. A layer 26 of an electrophoretic gel is adhered to one of the major surfaces 22 of the base sheet. In the preferred embodiment, the gel layer 26 is spaced apart from the peripheral edge 28 of the base sheet 20 so as to prevent contact of the gel layer with the container. The particular gel is not essential to the present invention and may include any of the mediums of the prior art mentioned hereinabove. However, agarose has been successfully utilized.

When the container 10 is closed by bending the container along the edge 18, a cavity 30 is formed within the container by the top portion 14 and the bottom portion 16, as illustrated in FIG. 4. The bottom portion 16 includes a bottom 17 and a recess 32 dimensioned such as to fully contain the support medium 12 therein. Along the edge of the bottom recess 32, a continuous or laterally and outwardly extending rim 34 protrudes or extends from the opposed sides 52, 54, back side 58 and front side 60 of the bottom portion 16 and surrounds the upwardly opening bottom recess 32. The rim 34 has a first leg 31 forming a horizontal surface parallel to and spaced from the bottom surface 62 of the bottom portion 16 and a second leg 33 forming a continuous vertical sealing surface 36 which is spaced from the sides 52, 54, 58 and 60 of the bottom portion 16. To insure that the top portion 14 does not come in contact with the gel layer 26, an additional and downwardly opening recess 40 is formed in the top portion 14 which includes a top 41 and depending side walls 43 perpendicularly connected to the top 41 and surrounding the recess 40. The side walls 43 of the top portion 14 terminate in a flange 45 having a first leg 47 forming a horizontal surface parallel to and spaced from the top 41 and a second leg 49 which includes a continuous vertical sealing surface 42 which contacts the continuous sealing surface 36 of the bottom recess 32 to provide a substantially air-type cavity 30 when the container 10 is enclosed.

As illustrated in FIG. 1, and in greater detail in FIGS. 2, 4 and 5, the electrophoretic support medium 12 is retained within the recess by a plurality of nubs 50. The nubs are generally spherical and protrude into the recess from the rim 34 along opposed sides 52 and 54 of the bottom portion recess 32 and are spaced apart from the bottom of the recess. The nubs 50 are engageable with the base sheet 20 when it is placed beneath the nubs and between the nubs and the bottom to be retained in the recess. Also, the nubs protrude into the recess a predetermined distance so as not to come in contact with the gel layer 26 spaced apart from the edge 28 of the base sheet 20. In the preferred embodiment, two additional nubs 56 protrude from the rim 34 along the back side 58 of the bottom portion recess. Thus, as illustrated in FIG. 5, the electrophoretic support medium may be slid into the recess 32 from the front side 60 under the side nubs 50. It should be appreciated that the use of the terms side, back and front are only relevant terms for discussion and are not essential to the present invention.

At least a portion of the bottom of the recess 32 of the bottom 17 portion 16 may include a substantially smooth planar surface 62. The surface should be substantially smooth to maximize contact between the other or exposed surface 24 of the base sheet 20 and the planar surface 62 of the bottom of the recess 32. This will assist in retaining the electrophoretic support medium 12 within the recess 12 because of the molecular attraction between the base sheet 20 and the bottom of the recess 32, which by itself would be insufficient.

The particular material of which the container 10 and base sheet 20 is made is not essential to the present invention. However, it has been found that polymeric materials, such as styrene for the container and Mylar for the base sheet ("MYLAR" is a trademark of E.I. DuPont de Nemours & Company of Wilmington, Del.), are satisfactory. Normally, the manufacturers of this product will select the best commercially available material based upon price, application and manufacturing process.

As illustrated in FIG. 1, a pair of valleys 64 are provided in recess 32. This substantially reduces air spaces and the like between the contacting surfaces to increase the retention of the support medium 12 within the recess 32. Further, an additional recess 68 is provided in the recess 32 beneath the plane of the planar surface 62 so that a person may place his or her finger beneath the base sheet 20 to remove the support medium 12 from the container 10.

As illustrated in FIG. 1, to facilitate opening of the container 10, the bottom portion 16 includes a tab 70, and the top portion 14 includes a tab 72. Thus, a person may grasp the tab 70 of the bottom portion with one hand, and the tab 72 of the top portion with the other hand, and by pulling easily open the container to expose the electrophoretic support medium retained therein.

There are several ways to produce the container 10 of the present invention which are known to those skilled in the art, such as vacuum forming. The particular manufacturing process is not essential to the present invention, and is a matter of choice based upon economics and availability.

While the preferred embodiment of the present invention has been described so as to enable one skilled in the art to practice the techniques of the present invention, the proceeding description is intended to be exemplary and should not be used to limit the scope of the invention. The scope of the inventon should be determined only by reference to the following claims.

We claim:

1. A container for protecting and enclosing an electrophoretic support medium having a base sheet with at least two opposed major surfaces and a layer of an electrophoretic gel adhered to one of the major surfaces of the base sheet, said container comprising:

a top portion, a bottom portion and a hinge portion between said top and bottom portions, all of said portions being integrally connected to permit relative movement between said top and bottom portions through the action of said hinge portions;

said bottom portion having an upwardly opening recess therein for accommodating the support medium, said bottom portion having a bottom, and two opposed sides, a back side and a front side which surrounds the recess and are perpendicularly connected to said bottom;

said bottom portion further including a laterally and outwardly extending rim having a first leg forming a surface parallel to and spaced from said bottom and a second leg forming a sealing surface which is spaced from and surround said two opposed sides, back side and front side;

said top portion having a downwardly opening recess therein, including a top and depending side walls perpendicularly connected to said top and surrounding the downwardly opening recess;

the side walls of said top portion terminating in a flange having a first leg forming a surface parallel to and spaced from said top and a second leg forming a sealing surface which is spaced from and surrounds said top side walls;

at least one nub protruding from each of the two opposed sides of said bottom portion into the recess provided therein, each nub being spaced apart from the bottom of said bottom portion, said nubs being engageable with the base sheet of the support medium so that when the support medium is placed in the recess between the nubs and the bottom of said bottom portion, the support medium is retained therein;

said top portion through the provision of said hinge portion being moveable relative to said bottom portion to bring the sealing surfaces of said rim and said flange into sealing engagement to thereby close the container.

2. The container defined in claim 1, further comprising at least one nub protruding from the back side of said bottom portion into the recess provided therein.

3. The container defined in claim 1, wherein at least a portion of said bottom further comprises a substantially smooth planar surface.

4. The container defined in claim 3, wherein the bottom of said bottom portion further comprises at least one valley, whereby air spaces between the base sheet of the support medium and the bottom of said bottom portion are substantially reduced.

5. The container defined in claim 1, wherein said bottom portion further comprises at least one additional recess adjacent said front side and communicating with said upwardly opening recess, said additional recess being located at least partially beneath the base sheet so that access to the base sheet may be gained to permit ease of removal of the base sheet and the layer of electrophoretic gel from said bottom portion.

6. The container defined in claim 1, wherein said top bottom and hinge portions are made of a polymeric material.

7. The container defined in claim 6, wherein the polymeric material is styrene.

8. The container defined in claim 1, wherein at least two nubs protrude from each of the two opposed sides of said bottom portion into the recess provided therein.

9. The container defined in claim 8, wherein at least two nubs protrude from the back side of said bottom portion into the recess provided therein.

10. The container defined in claim 1, wherein two nubs protrude from each opposed side and the back side of said bottom portion.

11. The container defined in claim 1, wherein the top portion and the bottom portion each further comprise a tab for assisting in opening the container.

* * * * *